(12) United States Patent
Aono et al.

(10) Patent No.: US 8,142,351 B2
(45) Date of Patent: Mar. 27, 2012

(54) ENDOSCOPE WITH MOVABLE OPTICAL MEMBER AND HEATING UNIT

(75) Inventors: Susumu Aono, Hachioji (JP); Mitsutaka Kokubo, Hachioji (JP)

(73) Assignee: Olympus Medical Systems Corp. (JP)

( * ) Notice: Subject to any disclaimer, the term of this patent is extended or adjusted under 35 U.S.C. 154(b) by 147 days.

(21) Appl. No.: 12/763,343

(22) Filed: Apr. 20, 2010

(65) Prior Publication Data

US 2010/0268027 A1     Oct. 21, 2010

Related U.S. Application Data

(63) Continuation of application No. PCT/JP2009/068286, filed on Oct. 23, 2009.

(30) Foreign Application Priority Data

Oct. 24, 2008     (JP) .................................. 2008-274486

(51) Int. Cl.
*A61B 1/05* (2006.01)
(52) U.S. Cl. ......... 600/167; 600/168; 600/169; 600/130
(58) Field of Classification Search .................. 600/129, 600/130, 167, 168, 169, 176
See application file for complete search history.

(56) References Cited

U.S. PATENT DOCUMENTS

| | | | | |
|---|---|---|---|---|
| 4,076,018 A | * | 2/1978 | Heckele | 600/168 |
| 4,182,547 A | * | 1/1980 | Siegmund | 385/117 |
| 5,605,532 A | * | 2/1997 | Schermerhorn | 600/169 |
| 7,125,378 B2 | * | 10/2006 | Shimizu et al. | 600/112 |
| 2007/0100209 A1 | * | 5/2007 | Takahashi | 600/167 |
| 2007/0149856 A1 | * | 6/2007 | Segawa | 600/169 |
| 2008/0194914 A1 | * | 8/2008 | Iwasaki | 600/167 |
| 2009/0076332 A1 | * | 3/2009 | Iwasaki et al. | 600/168 |
| 2010/0010313 A1 | * | 1/2010 | Muckner et al. | 600/169 |

FOREIGN PATENT DOCUMENTS

EP     1 955 645     8/2008

(Continued)

OTHER PUBLICATIONS

English translation of International Search Report issued on Jan. 26, 2010 in connection with corresponding PCT application No. PCT/JP2009/068286.

(Continued)

*Primary Examiner* — John P Leubecker
(74) *Attorney, Agent, or Firm* — Ostrolenk Faber LLP

(57) ABSTRACT

An endoscope insertion portion includes an imaging unit including a distal end optical member arranged at a distal end portion of the imaging unit and a movable optical member configured to be moved relative to the distal end optical member, an actuator unit arranged in a position relative to the distal end optical member, configured to drive the movable optical member and including a shape memory member configured to deform according to temperature, and a heater unit including a heating member configured to heat the distal end optical member wherein the heater unit is arranged on one side opposite to other side on which the actuator unit is arranged and the heating member is configured to heat the distal end optical member from the one side to the other side, relative to the optical axis of the imaging unit, when viewing in the axial direction of the insertion portion.

7 Claims, 5 Drawing Sheets

FOREIGN PATENT DOCUMENTS

| | | |
|---|---|---|
| EP | 2 311 365 | 4/2011 |
| JP | 2-257926 | 10/1990 |
| JP | 5-337078 | 12/1993 |
| JP | 11-047080 | 2/1999 |
| JP | 2007-229155 | 9/2007 |
| JP | 2008-023275 | 2/2008 |
| JP | 2008-079823 | 4/2008 |

OTHER PUBLICATIONS

Search Report issued by European Patent Office in connection with corresponding application No. EP 09 82 2093 on Aug. 5, 2011.

International Search Report and Written Opinion mailed Jan. 26, 2010 in corresponding PCT International Application No. PCT/JP2009/068286.

* cited by examiner

ENDOSCOPE WITH MOVABLE OPTICAL MEMBER AND HEATING UNIT

CROSS-REFERENCE TO RELATED APPLICATIONS

This is a Continuation Application of PCT Application No. PCT/JP2009/068286, filed Oct. 23, 2009, which was published under PCT Article 21(2) in Japanese.

This application is based upon and claims the benefit of priority from prior Japanese Patent Application No. 2008-274486, filed Oct. 24, 2008, the entire contents of which are incorporated herein by reference.

BACKGROUND OF THE INVENTION

1. Field of the Invention

The present invention relates to an endoscope insertion portion using an actuator unit and a heater unit together for an imaging unit wherein a shape memory member is used in the actuator unit in order to drive a movable optical member of the imaging unit, which is configured to deform according to the temperature and a heating member is used in the heater unit, which is configured to heat a distal end optical member of the imaging unit.

2. Description of the Related Art

In Jpn. Pat. Appln. KOKAI Publication No. 2007-219155, one example of an actuator unit is disclosed. In an endoscope disclosed in Jpn. Pat. Appln. KOKAI Publication No. 2007-219155, an imaging unit is provided at the distal end portion of the endoscope. The imaging unit includes a movable lens frame with a group of objective lenses assembled therein and movable in an optical axial direction. The movable lens frame is configured to be driven by an actuator unit, and a shape memory alloy (which is referred to as SMA, hereinafter) wire is used in the actuator unit.

In Jpn. Pat. Appln. KOKAI Publication No. 11-47080, one example of a heater unit is disclosed. In an endoscope disclosed in Jpn. Pat. Appln. KOKAI Publication No. 11-47080, a heating body is provided so as to enclose the outer periphery of an objective optical system in the distal end portion of the endoscope. Heat produced in the heating body is transmitted to the objective optical system, and the objective optical system rises in the temperature, and therefore, the objective optical system is prevented from being fogged.

BRIEF SUMMARY OF THE INVENTION

In an aspect of the present invention, an endoscope insertion portion extends in an axial direction and includes: an imaging unit configured to acquire an observation image and including a distal end optical member arranged at a distal end portion of the imaging unit and a movable optical member configured to be moved relative to the distal end optical member, and having an optical axis; an actuator unit arranged in a position relative to the distal end optical member, configured to drive the movable optical member and including a shape memory member configured to deform according to temperature; and a heater unit including a heating member configured to heat the distal end optical member wherein the heater unit is arranged on one side opposite to other side on which the actuator unit is arranged and the heating member is configured to heat the distal end optical member from the one side opposite to the other side on which the actuator unit is arranged to the other side on which the actuator unit is arranged, relative to the optical axis of the imaging unit, when viewing in the axial direction of the insertion portion.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
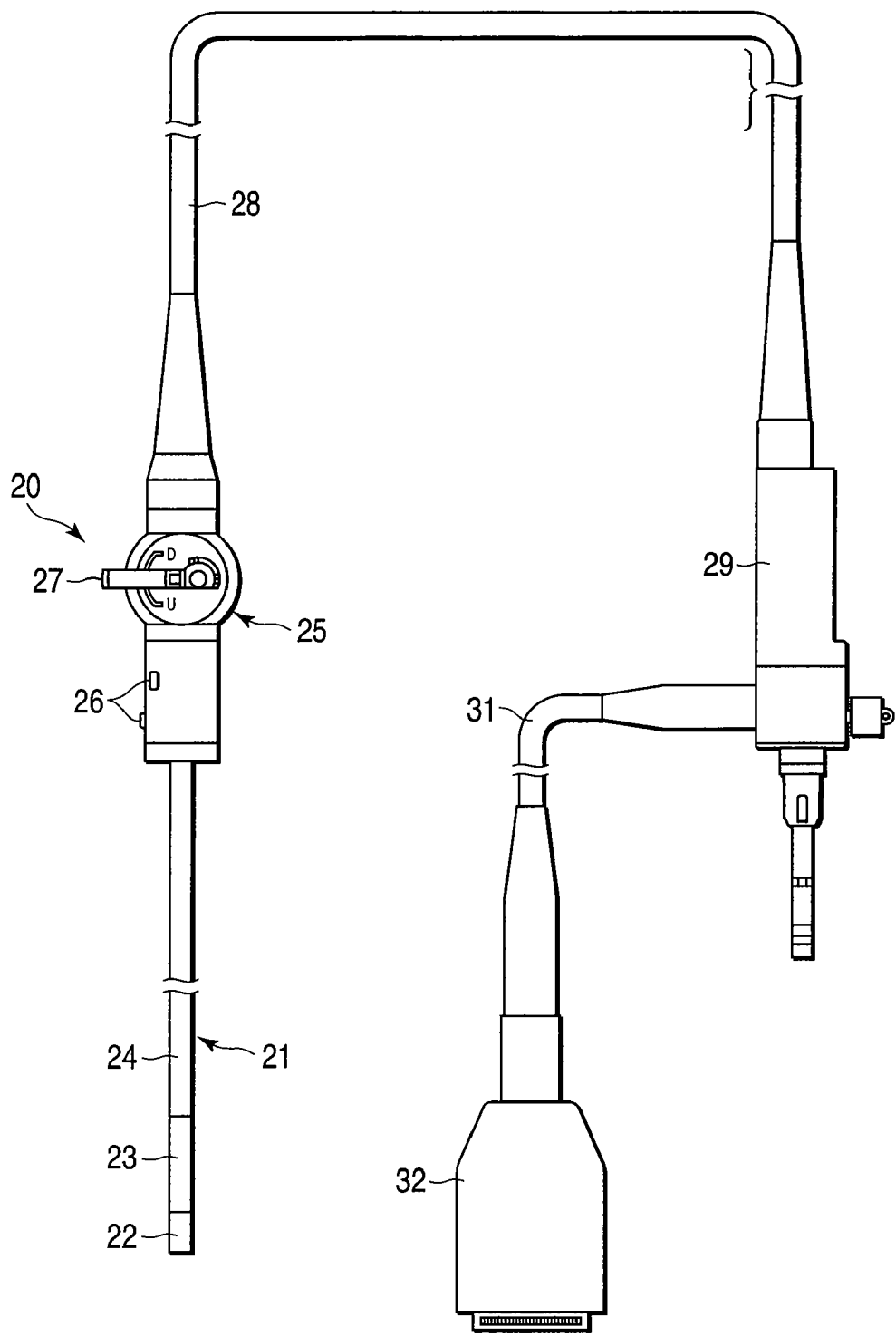
FIG. 1 is a side view showing an endoscope according to an embodiment of the present invention.

An embodiment of the present invention will be explained referring to the drawings.

Referring to FIG. 1, an endoscope 20 includes an insertion portion 21 configured to be inserted into a body. In the insertion portion 21, a distal end rigid portion 22 being rigid, a bending portion 23 operated to be bent, and a flexible tube portion 24 being long and flexible are provided from the distal end side to the proximal end side. An operation portion 25 is coupled to the proximal end portion of the insertion portion 21 and is configured to be held and operated by an operator. Various switches 26 and a bending operation lever 27 are provided in the operation portion 25 and the bending operation lever 27 is configured to operate the bending portion 23 to be bent. A universal cable 28 extends from the operation portion 25, and a light source connector 29 is provided at the extending end portion of the universal cable 28. Moreover, an electrical cable 31 extends from the light source connector 29, and an electrical connecter 32 is provided at the extending end portion of the electrical cable 31. The light source connector 29 and the electrical connecter 32 are connected with a light source apparatus and a video processor, respectively.

Hereinafter, various units of the insertion portion 21 will be explained in detail.

Here, the insertion portion 21 extends in the axial direction, two directions which are orthogonal to the axial direction of the insertion portion 21 and each other are referred to as up and down direction, and left and right direction, respectively. In FIGS. 2 to 8, up, down, left and right are referred to as U, D, L and R, respectively.

Figure 2:
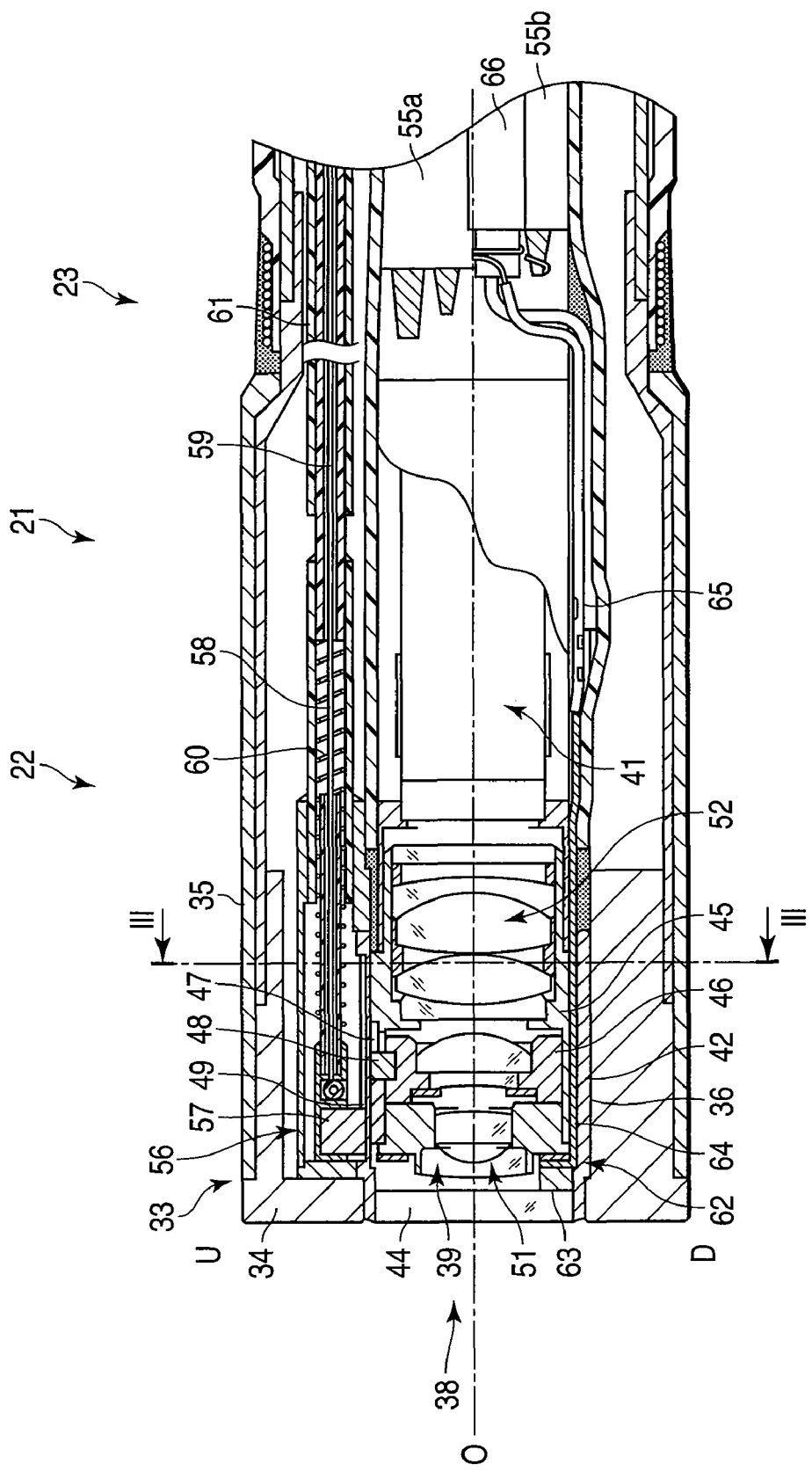
FIG. 2 is a longitudinally cross-sectional view showing the distal end portion of an insertion portion according to the embodiment of the present invention.
Figure 3:
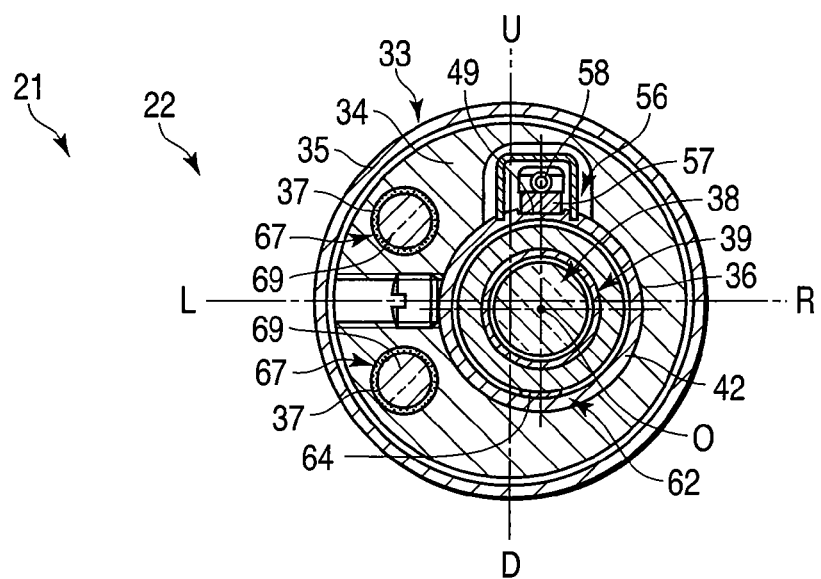
FIG. 3 is a transversally cross-sectional view showing the distal end portion of the insertion portion according to the embodiment of the present invention along III-III line in FIG. 2.
Figure 4:
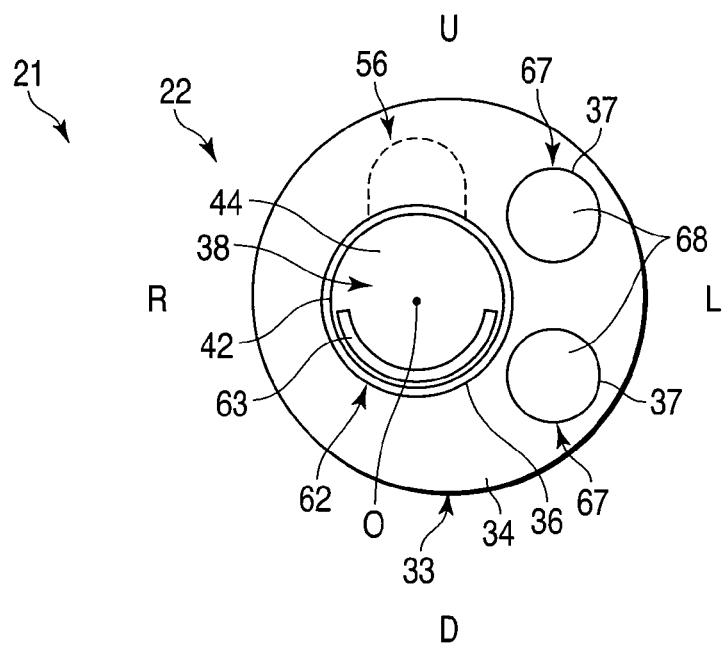
FIG. 4 is a front view showing the distal end portion of the insertion portion according to the embodiment of the present invention.

Referring to FIGS. 2 to 4, an exterior unit 33 is provided in the distal end rigid portion 22 and forms an outer frame of the distal end rigid portion 22. The exterior unit 33 is formed by a distal end side exterior member 34 and a proximal end side exterior member 35, the distal end side exterior member 34 has a shape of a short circular column and the proximal end side exterior member 35 has a shape of a circular cylinder, and the distal end portion of the proximal end side exterior member 35 is coaxially fitted on the outside of and fixed to the proximal end side part of the distal end side exterior member 34. An imaging bore 36 and an illumination bore 37 penetrate the distal end side exterior member 34 in the axial direction.

Referring to FIGS. 2 to 7, an imaging unit 38 is provided within the exterior unit 33 and configured to acquire an observation image. The imaging unit 38 extends in the axial direction of the insertion portion 21. The central axis of the imaging unit 38 agrees with an optical axis O of the imaging unit 38 and arranged a little lower with respect to the up and down direction and on the right side with respect to the left and right direction relative to the central axis of the insertion portion 21. The imaging unit 38 is formed by an objective optical unit 39 on the distal end side and an image pick-up optical unit 41 on the proximal end side.

Referring to FIGS. 2 to 4, the objective optical unit 39 includes a circular cylindrical outer lens frame 42 as a supporting member. The outer lens frame 42 is made of a material having low thermal conductivity, for example, polyphenylsulfone, PEEK, polysulfone, polyethylene, stainless steel and has a heat-insulating function. The outer lens frame 42 is fitted on the inside of the imaging bore 36 of the distal end side exterior member 34 and fixed to the distal end side exterior member 34 with a fixing screw 43. An objective cover lens 44 as a distal end optical member is fitted on the inside of and fixed to the distal end portion of the outer lens frame 42. The distal end surface of the objective cover lens 44 is substantially coplanar with the distal end surface of the distal end side exterior member 34 and exposed outside. The distal end surface of the objective cover lens 44 may be fogged when the insertion portion 21 is inserted into the body because body temperature is generally higher than room temperature. An interior lens frame 45 is fitted on the inside of and fixed to the proximal end side part of the outer lens frame 42. A movable lens frame 46 is inserted into the distal end side part of the interior lens frame 45 so as to be movable in the axial direction relative to the interior lens frame 45. That is, a penetrating groove-shaped guide groove 47 extends in the axial direction on the upper position in the distal end side part of the interior lens frame 45, a guide pin 48 protrudes upward from the upper end portion of the outer peripheral portion of the movable lens frame 46, and the guide pin 48 of the movable lens frame 46 is inserted into the guide groove 47 of the interior lens frame 45 so as to be slidable in the axial direction. In order to drive the movable lens frame 46, the guide pin 48 is made of a magnetic material such as a metal, and a concave groove-shaped driving groove 49 extends in the axial direction on the upper position of the outer peripheral portion of the distal end side part of the outer lens frame 42. A distal end side group of objective lenses 51 as a movable optical member is fitted on the inside of and fixed to the movable lens frame 46. A proximal end side group of objective lenses 52 is fitted on the inside of and fixed to the proximal end side part of the interior lens frame 45.

An image formation of an observation image is performed by the objective cover lens 44, the distal end side group of objective lenses 51 and the proximal end side group of objective lenses 52 in the objective optical unit 39. Here, it is possible to perform focusing by moving the movable lens frame 46 in the optical axial direction to move the distal end side group of objective lenses 51 in the optical axial direction.

Figure 5:
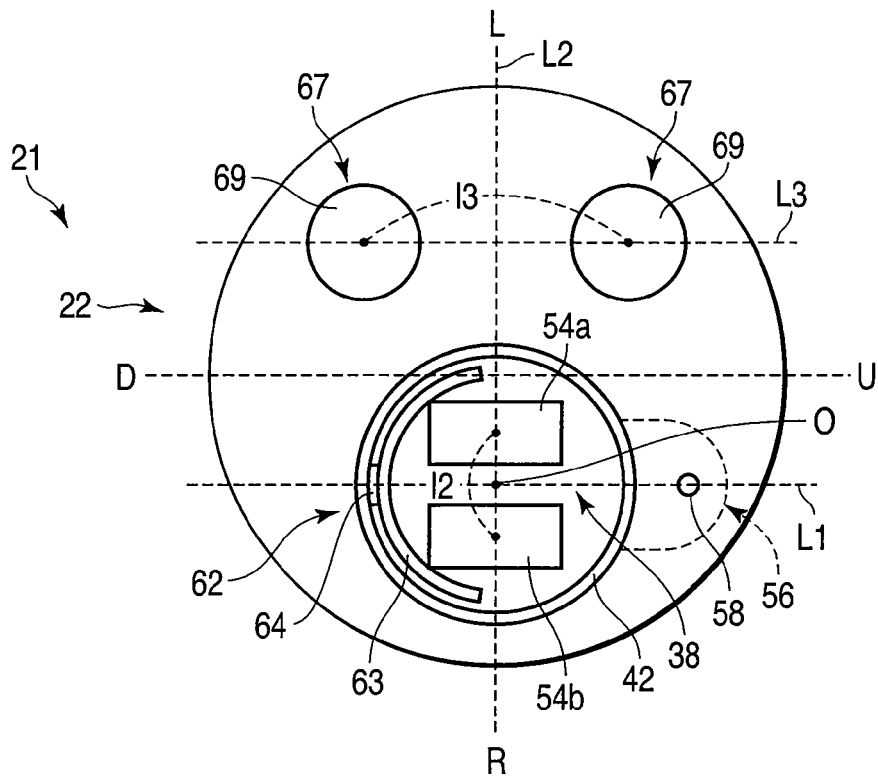
FIG. 5 is a schematic view showing the distal end portion of the insertion portion according to the embodiment of the present invention when viewing in the axial direction.
Figure 6:
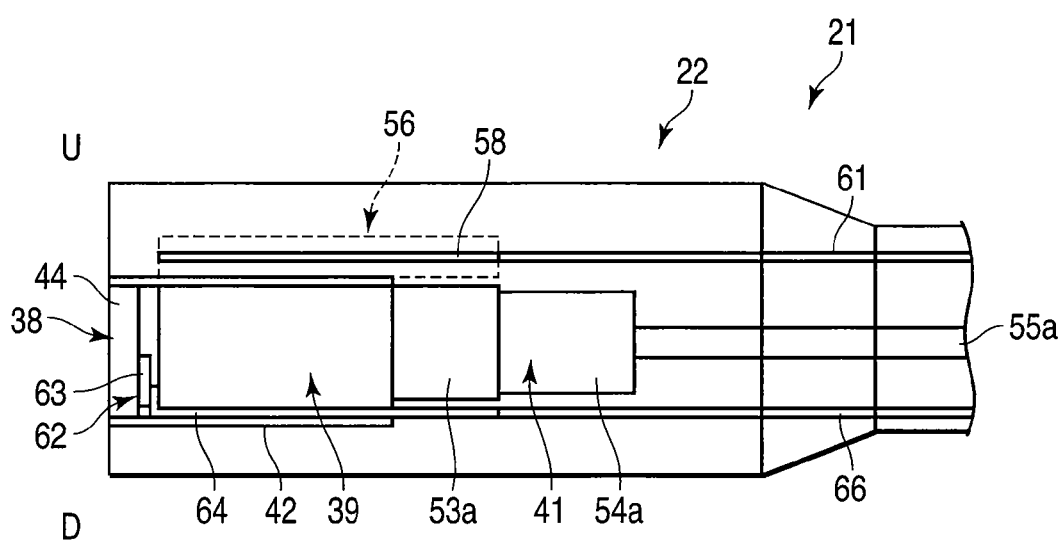
FIG. 6 is a schematic longitudinally cross-sectional view showing the distal end portion of the insertion portion according to the embodiment of the present invention when viewing in the left and right direction.
Figure 7:
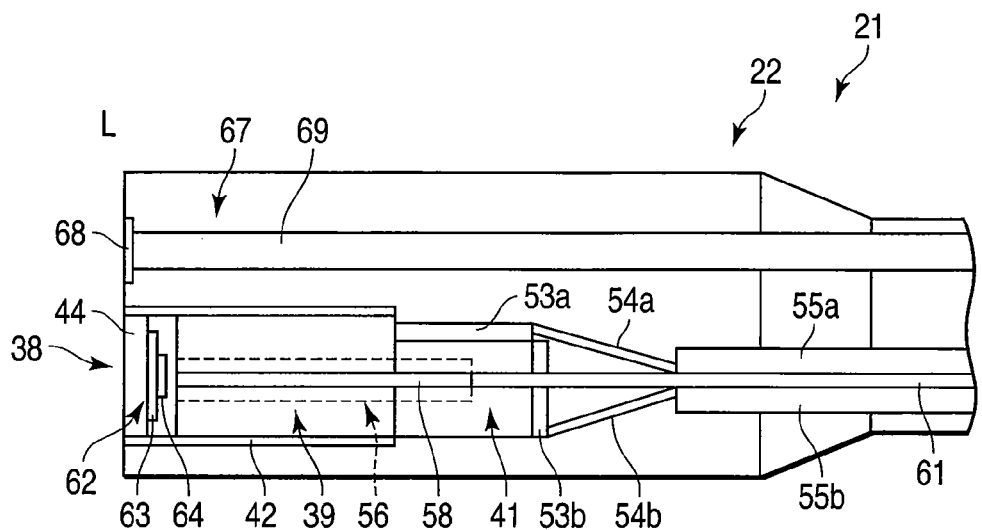
FIG. 7 is a schematic longitudinally cross-sectional view showing the distal end portion of the insertion portion according to the embodiment of the present invention when viewing in the up and down direction.

Referring to FIGS. 5 to 7, in the image pick-up optical unit 41 according to the present embodiment, a CCD for red and blue and a CCD for green with a large number of picture elements are used as an imaging device in order to obtain a high-definition image and improve a color reproduction quality. The one CCD 53a is arranged on the left side part of the image pick-up optical unit 41 and orthogonal to the left and right direction, and the other CCD 53b is arranged on the proximal end side of the one CCD 53a and orthogonal to the axial direction. A CCD substrate 54a, 54b as an imaging substrate is coupled to each CCD 53a, 53b. Both the CCD substrates 54a and 54b are inclined relative to the central axis of the imaging unit 38 and arranged on the left side and the right side, respectively, symmetrically with each other relative to the central axis. Regarding an opposite surface arranged on the side opposite to the central axis of the imaging unit 38, the opposite surface of the one CCD substrate 54a is directed leftward and proximally and the opposite surface of the other CCD substrate 54b is directed rightward and proximally. Here, various signal lines extend from the CCD substrates 54a and 54b, and the various signal lines are integrated into the image pick-up cables 55a and 55b. Two image pick-up cables 55a and 55b are used for the two CCDs 53a and 53b and CCD substrates 54a and 54b, respectively.

When the electrical connecter 32 of the endoscope 20 is connected to the video processor and the CCDs 53a and 53b and the CCD substrates 54a and 54b are operated by the video processor, the CCDs 53a and 53b and the CCD substrates 54a and 54b acquire an observation image and produce an image signal. The produced image signal is output to the video processor, and an observation image is displayed on the video processor. When the imaging unit 38 is operated, the CCDs 53a and 53b and the CCD substrates 54a and 54b produce heat. On the one hand, the operation of the CCDs 53a and 53b and the CCD substrates 54a and 54b may be easily influenced by heat from the outside, and an image is degraded because of the influence of the heat from the outside. Moreover, the operation of the CCD substrates 54a and 54b may be easily influenced by electrical noise from the outside, and an image is degraded because of the influence of the electrical noise.

Referring to FIGS. 2 to 4, an actuator unit 56 is provided within the exterior unit 33 and configured to drive the distal end side group of objective lenses 51 of the imaging unit 38. That is, the actuator unit 56 extends in the axial direction on the upper side of the imaging unit 38 along the imaging unit 38. The actuator unit 56 includes a driving magnet 57. The driving magnet 57 is arranged in the driving groove 49 of the outer lens frame 42 of the objective optical unit 39 so as to be slidable in the axial direction. The driving magnet 57 is magnetically coupled to the guide pin 48 of the movable lens frame 46 of the objective optical unit 39. When the driving magnet 57 is moved in the axial direction, the guide pin 48 is moved in the axial direction, and then, the movable lens frame 46 is moved in the optical axial direction. A reset spring 60 always distally urges the driving magnet 57. Moreover, the distal end portion of a SMA wire 58 as a shape memory member is coupled to the driving magnet 57. The SMA wire 58 extends in the axial direction. The distal end portion of a current line 59 is connected to the proximal end portion of the SMA wire 58, and the proximal end portion of the SMA wire 58 is held so as to be unmovable in the axial direction. Here, the current line 59 is put into an actuator cable 61, and the actuator cable 61 is inserted through the bending portion 23 and extends to the electrical connecter 32.

When an electric current flows through the SMA wire 58 via the current line 59 and the temperature of the SMA wire 58 becomes higher than the transformation temperature, the SMA wire 58 is deformed to shrink in the axial direction against the urging force of the reset spring 60 to move the driving magnet 57 proximally. On the other hand, when the electric current is stopped from flowing through the SMA wire 58 and the temperature of the SMA wire 58 become lower than the transformation temperature, the SMA wire 58 is deformed to expand in the axial direction and the driving magnet 57 is moved distally by the urging force of the reset spring 60. That is, when the actuator unit 56 is operated, the SMA wire 58 produces heat. On the other hand, the operation of the SMA wire 58 is influenced by heat from the outside, and the SMA wire 58 may not suitably operate because of the influence of the heat from the outside. In this case, the driving magnet 57 and the movable lens frame 46 are not suitably moved, and then, an obtained observation image may be out of focus.

Referring to FIGS. 2 to 4, a heater unit 62 is provided within the exterior unit 33 and configured to heat the objective cover lens 44 of the imaging unit 38. That is, the heater unit 62 extends in the axial direction along the imaging unit 38 on the lower end part of the imaging unit 38. The heater unit 62 includes a heating element 63 as a heating member. The heating element 63 is provided on the lower end part of the proximal end side of the objective cover lens 44. In the present embodiment, the heating element 63 is in contact with the proximal end surface of the objective cover lens 44 and has a shape of a belt extending along the periphery and over substantially half the circumference in the lower semicircular part of the proximal end surface. Here, the heating element 63 may not be in contact with the objective cover lens 44, and the shape of the heating element 63 may be set on any shape such as a shape of a semicircle or a crescent. The heating element 63 is connected to the one end portion of a heater substrate 64 being a flexible substrate. The heater substrate 64 is arranged between the interior lens frame 45 and the outer lens frame 42 and extends in the axial direction on the lower position of the inner peripheral portion of the outer lens frame 42. The distal end portion of a power line 65 is connected to the proximal end portion of the heater substrate 64. Here, the power line 65 is integrated into a heater cable 66, and the heater cable 66 is inserted through the bending portion 23 and extends to the electrical connecter 32.

When the heater substrate 64 and the heating element 63 are supplied with electrical power via the power line 65 and the heating element 63 is heated, the objective cover lens 44 rises in the temperature and is prevented from being fogged. When the heater unit 62 is operated, the heating element 63 produces heat, and further, the heater substrate 64 produces heat. Here, noise may be produced in an electric signal transmitted through the power line 65 because of influence of electrical noise from the outside.

Referring to FIGS. 3, 4 and 7, an illumination unit 67 is provided within the insertion portion 21 and configured to illuminate an object of observation. That is, an illumination lens 68 as an emitting member is provided at the distal end portion of the illumination bore 37 of the distal end side exterior member 34. Moreover, the distal end portion of a light guide 69 as a transmitting member is inserted through and fixed to the illumination bore 37. The distal end surface of the light guide 69 is joined to the proximal end surface of the illumination lens 68. In the present embodiment, two illumination units 67 are used, and the two illumination units 67 are arranged on the upper side with respect to the up and down direction and on the left side and the right side with respect to the left and right direction, respectively, symmetrically with each other relative to the central axis of the insertion portion 21 within the exterior unit 33. The light guide 69 extends from the distal end side exterior member 34, is inserted through the bending portion 23, and extends to the light source connecter 29.

The light source connecter 29 of the endoscope 20 is connected to the light source apparatus, and illumination light produced in the light source apparatus is transmitted through the light guide 69, supplied to the illumination lens 68, and emitted from the illumination lens 68 to an object of observation. When the illumination light is transmitted through the illumination unit 67, a loss of an amount of light is caused and the illumination unit 67 produces heat. In particular, in the interface between the distal end surface of the light guide 69 and the proximal end surface of the illumination lens 68, a large loss of an amount of light, and then, a large amount of heat are caused. Moreover, in the present embodiment, an amount of light for the illumination light is increased because the two CCDs 53a and 53b with a large number of picture elements are used for acquiring an observation image, and then, the CCDs 53a, 53b lower in sensitivity and an image become dark. Therefore, an amount of heat in the illumination unit 67 becomes large.

As is described in detail below, in the present embodiment, the various units are arranged in the insertion portion 21 so as to minimize relative influence of heat, and therefore, suitable operation of the various units is ensured.

Referring to FIGS. 2 to 4, during operation of the heater unit 62, the heating element 63 and the heater substrate 64 produce heat, and therefore, the SMA wire 58 of the actuator unit 56 is influenced by the heat produced in the heating element 63 and the heater substrate 64 and may not suitably operate. In the present embodiment, the actuator unit 56 is arranged on the upper position and the heater unit 62 is arranged on the lower position relative to the optical axis O of the imaging unit 38, namely, the actuator unit 56 and the heater unit 62 are arranged opposite to each other relative to the optical axis O of the imaging unit 38, when viewing in the axial direction of the insertion portion 21. That is, the actuator unit 56 and the heater unit 62 are arranged as apart as possible within permissible limits for their functions when viewing in the axial direction of the insertion portion 21. Therefore, the SMA wire 58 is hardly influenced by the heat produced in the heating element 63 and the heater substrate 64. Moreover, the actuator unit 56 is arranged on the outside of the outer lens frame 42 and the heater unit 62 is arranged on the inside of the outer lens frame 42, namely, the outer lens frame 42 having the heat-insulating function is arranged between the actuator unit 56 and the heater unit 62. Therefore, the SMA wire 58 is more hardly influenced by the heat produced in the heating element 63 and the heater substrate 64, and then, suitable operation of the actuator unit 56 is ensured.

Here, the heater unit 62 is arranged on the inside of the outer lens frame 42 and the outer lens frame 42 is fitted on the inside of and fixed to the imaging bore 36 of the distal end side exterior member 34, namely, the outer lens frame 42 having the heat-insulating function is arranged between the heater unit 62 and the exterior unit 33. Therefore, during operation of the heater unit 62, the exterior unit 33 is prevented from rising in the temperature by the heat produced in the heating element 63 and the heater substrate 64.

Referring to FIG. 5, during operation of the imaging unit 38, the CCD substrates 54a and 54b produces heat, and therefore, the SMA wire 58 of the actuator unit 56 is influenced by the heat produced in the CCD substrates 54a and 54b and may not suitably operate. On the other hand, during operation of the heater unit 62 and the actuator unit 56, the heating element 63 and the heater substrate 64, and the SMA wire 58 produce heat, and therefore, the CCD substrates 54a and 54b of the imaging unit 38 is influenced by the heat produced in the heating element 63 and the heater substrate 64, and the SMA wire 58 and may not suitably operate. In the present embodiment, the two CCD substrates 54a and 54b are arranged on the left side and the right side symmetrically with each other relative to the central axis of the imaging unit 38, and the straight line L1 connecting the centers of heating of the actuator unit 56 and the heater unit 62 with each other is a perpendicular bisector of line segment L2 connecting the centers of heating of the two CCD substrates 54a and 54b, when viewing in the axial direction of the insertion portion 21. That is, the actuator unit 56 and the two CCD substrates 54a and 54b, and the heater unit 62 and the two CCD substrates 54a and 54b are arranged as apart as possible within permissible limits for their functions, when viewing in the axial direction of the insertion portion 21. Therefore, the SMA wire 58 is hardly influenced by the heat produced in the two CCD substrates 54a and 54b and the two CCD substrates 54a and 54b is hardly influenced by the heat produced in the SMA wire 58, the heating element 63 and the heater substrate 64, and therefore, suitable operation of the actuator unit 56 and the imaging unit 38 is ensured.

Here, when a high-frequency treatment instrument configured to treat a living tissue with a high-frequency current together with the endoscope, noise may be caused in an electric signal transmitting through the power line 65 of the heater cable 66 because of the high-frequency current and influence the CCD substrates 54a and 54b, and then, an image may be degraded. As is described above, in the present embodiment, the heater unit 62 and the two CCD substrates 54a and 54b are arranged as apart as possible within permissible limits for their functions when viewing in the axial direction of the insertion portion 21, and the heater cable 66 extending from the heater unit 62 in the axial direction is also arranged as apart as possible within permissible limits for their functions relative to the two CCD substrates 54a and 54b, when viewing in the axial direction of the insertion portion 21. Therefore, the CCD substrates 54a and 54b are hardly influenced by the noise of the electrical signal transmitting through the power line 65 of the heater cable 66, and suitable operation of the imaging unit 38 is ensured.

Referring to FIG. 5, during operation of the illumination units 67, the illumination units 67 produce heat, and therefore, the SMA wire 58 of the actuator unit 56 and the CCD substrates 54a and 54b of the imaging unit 38 are influenced and may not suitably operate. In the present embodiment, the two illumination units 67 are arranged on the left side with respect to the left and right direction and on the upper side and the lower side with respect to the up and down direction, respectively, symmetrically with each other relative to the central axis of the insertion portion 21 within the exterior unit 33, and the straight line L2 connecting the centers of heating of the two CCD substrates 54a and 54b is a perpendicular bisector of line segment L3 connecting the centers of heating of the two illumination units 67 when viewing in the axial direction of the insertion portion 21. That is, the actuator unit 56 and the two illumination units 67, and the two CCD substrates 54a and 54b and the two illumination units 67 are arranged as apart as possible within permissible limits for their functions, respectively, when viewing in the axial direction of the insertion portion 21. Therefore, the SMA wire 58 and the two CCD substrates 54a and 54b are hardly influenced by heat produced in the two illumination units 67, and therefore, suitable operation of the actuator unit 56 and the imaging unit 38 is ensured.

Referring to FIGS. 6 and 7, during operation of the actuator unit 56, the SMA wire 58 produces heat, during operation of the heater unit 62, in particular, the heating element 63 produces heat, during operation of the imaging unit 38, the CCDs 53a and 53b and the CCD substrates 54a and 54b produces heat, and during operation of the illumination unit 67, in particular, the interface between the illumination lens 68 and the light guide 69 produces heat. The SMA wire 58, the CCDs 53a and 53b, and the CCD substrates 54a and 54b may not suitably operate because of the influence of the heat produced in the other heating portion. In the present embodiment, the interface between the illumination lens 68 and the light guide 69, the heating element 63, the SMA wire 58, the CCDs 53a and 53b and the CCD substrates 54a and 54b are arranged in order from the distal end side to the proximal end side on the positions different from one another, respectively, with respect to the axial direction of the insertion portion 21. Therefore, the SMA wire 58, the CCDs 53a and 53b and the CCD substrates 54a and 54b are hardly influenced by the heat produced in the other heating portion, and then, suitable operation of the actuator unit 56 and the imaging unit 38 is ensured.

Here, the SMA wire 58, the CCDs 53a and 53b and the CCD substrates 54a and 54b, the heating element 63 and the heater substrate 64, and the illumination units 67 may be increased in an amount of heat because of the influence of the other heating portion and, as a result, the whole distal end rigid portion 22 and then the exterior unit 33 may rise in the temperature. In the present embodiment, as is described above, the SMA wire 58, the CCDs 53a and 53b and the CCD substrates 54a and 54b, the heating element 63 and the heater substrate 64, and the illumination units 67 are arranged so as to be influenced by the heat produced in the other heating portion as less as possible, and therefore, the exterior unit 33 is prevented from rising in the temperature.

Figure 8:
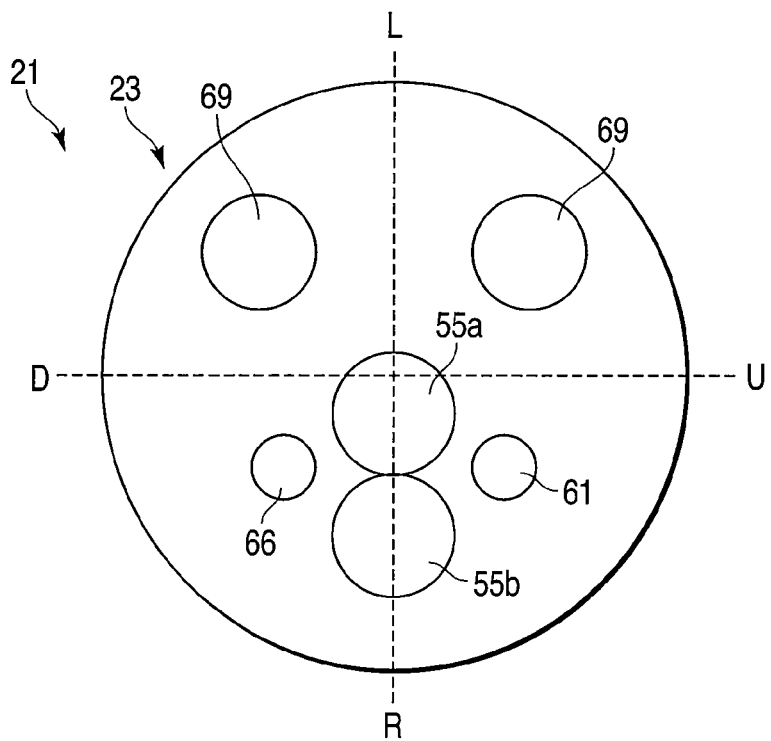
FIG. 8 is a schematic transversally cross-sectional view showing a bending portion according to the embodiment of the present invention when viewing in the axial direction.

As is mentioned above, in the present embodiment, the various units are arranged so as to minimize the relative influence of the heating. As a result, as is shown in FIG. 5, the two light guides 69, and the actuator unit 56 and the heater unit 62 are arranged side by side in the left and right direction, respectively, and the straight line L3 connecting the centers of the two light guides 69 with each other and the straight line L1 connecting the centers of the actuator unit 56 and the heater unit 62 with each other are parallel to each other, when viewing in the axial direction of the insertion portion 21. Therefore, the space within the exterior unit 33 is made maximally efficient use of. Moreover, during bending operation in the up and down direction, the actuator unit 56 and the heater unit 62 are prevented from applying unnecessary load to the light guide 69. Furthermore, as is shown in FIG. 8, the light guide 69 of the illumination unit 67 and the various cables 55a, 55b, 61 and 66 extending from the various units 38, 56 and 62 are arranged evenly on the upper side, the lower side, the left side and the right side relative to the central axis of the bending portion 23 within the bending portion 23. Therefore, during bending operation of the bending portion 23, it is prevented that the bending portion 23 meanders because of unevenness of the built-in members.

In the above embodiment, although the actuator unit 56 and the heater unit 62 are arranged opposite to each other relative to the optical axis O of the imaging unit 38, the actuator unit and the heater unit may be arranged simply on the sides opposite to each other, respectively, relative to the central axis of the imaging unit 38, when viewing in the axial direction of the insertion portion 21. Furthermore, one or more actuator unit 56 and one or more heater unit 62 may be arranged on the sides opposite to each other, respectively, relative to the optical axis O of the imaging unit 38 when viewing in the axial direction of the insertion portion 21.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope insertion portion,
wherein the endoscope insertion portion extends in an axial direction and comprises:
an exterior unit forming an outer frame of a distal end portion of the insertion portion;
an imaging unit provided within the exterior unit, extending in the axial direction, configured to acquire an observation image and including a cylindrical supporting member which extends in the axial direction and has a heat-insulating function, a distal end optical member which is arranged at a distal end portion of the supporting member within the supporting member and a movable optical member which is configured to be moved in the axial direction relative to the distal end optical member, and having an optical axis;
an actuator unit provided within the supporting member, arranged at an outer peripheral surface portion of the supporting member, extending in the axial direction, configured to drive the movable optical member and including a shape memory member which is configured to deform according to temperature; and
a heater unit provided within the supporting member, arranged at an inner peripheral surface portion of the supporting member, extending in the axial direction, arranged on a side opposite to a side on which the actuator unit is arranged relative to the optical axis of the imaging unit when viewing in the axial direction of the insertion portion, configured to heat the distal end optical member and including a heating member which is thermally connected to a proximal end side portion of the distal end optical member on the side opposite to the side on which the actuator unit is arranged relative to the optical axis of the imaging unit when viewing in the axial direction of the insertion portion and is configured to produce heat.

2. The endoscope insertion portion according to claim 1,
wherein the imaging unit includes two imaging substrates, and
a straight line connecting the actuator unit and the heater unit with each other is substantially a perpendicular bisector of a line segment connecting the two imaging substrates with each other, when viewing in the axial direction of the insertion portion.

3. The endoscope insertion portion according to claim 2,
wherein the endoscope insertion portion further comprising two illumination units configured to supply illumination light to an object of observation, and
a straight line connecting the two imaging substrates with each other is substantially a perpendicular bisector of a line segment connecting the two illumination units with each other, when viewing in the axial direction of the insertion portion.

4. The endoscope insertion portion according to claim 1,
wherein the shape memory member and the heating member are arranged in positions different from each other with respect to the axial direction of the insertion portion, respectively.

5. The endoscope insertion portion according to claim 4,
wherein the imaging unit includes an imaging device and an imaging substrate, and
the shape memory member, the heating member, and the imaging device and the imaging substrate are arranged in positions different from one another with respect to the axial direction of the insertion portion, respectively.

6. The endoscope insertion portion according to claim 5,
wherein the endoscope insertion portion further comprising an illumination unit configured to supply illumination light to an object of observation,
the illumination unit includes: a transmitting member configured to transmit the illumination light; and an emitting member connected with an end portion of the transmitting member and configured to emit the illumination light transmitted by the transmitting member to the object of observation, and
the shape memory member, the imaging device and the imaging substrate, and a connecting portion of the transmitting member and the emitting member are arranged in positions different from one another with respect to the axial direction of the insertion portion, respectively.

7. The endoscope insertion portion according to claim 1,
wherein the actuator unit includes a driving member arranged at the outer peripheral surface portion of the supporting member and being movable in the axial direction by the shape memory member,
the imaging unit includes a driven member arranged at the inner peripheral surface portion of the supporting member, provided at the movable optical member and being movable in the axial direction together with the movable optical member, and
the driven member is magnetically coupled to the driving member and configured to be moved in the axial direction by an axial movement of the driving member.

* * * * *